US011137506B2

(12) United States Patent
Park

(10) Patent No.: US 11,137,506 B2
(45) Date of Patent: Oct. 5, 2021

(54) POSITRON TOMOGRAPHY DEVICE USING MICROPATTERN DETECTOR

(71) Applicant: UNIVERSITY OF SEOUL INDUSTRY COOPERATION FOUNDATION, Seoul (KR)

(72) Inventor: Inkyu Park, Seoul (KR)

(73) Assignee: UNIVERSITY OF SEOUL INDUSTRY COOPERATION FOUNDATION, Seoul (KR)

( * ) Notice: Subject to any disclaimer, the term of this patent is extended or adjusted under 35 U.S.C. 154(b) by 0 days.

(21) Appl. No.: 16/754,900

(22) PCT Filed: May 10, 2018

(86) PCT No.: PCT/KR2018/005402
§ 371 (c)(1),
(2) Date: Apr. 9, 2020

(87) PCT Pub. No.: WO2019/098472
PCT Pub. Date: May 23, 2019

(65) Prior Publication Data
US 2020/0271799 A1 Aug. 27, 2020

(30) Foreign Application Priority Data
Nov. 14, 2017 (KR) .................. 10-2017-0151244

(51) Int. Cl.
*G01T 1/29* (2006.01)
*A61B 6/03* (2006.01)
*A61B 6/00* (2006.01)

(52) U.S. Cl.
CPC ............ *G01T 1/2985* (2013.01); *A61B 6/037* (2013.01); *A61B 6/508* (2013.01)

(58) Field of Classification Search
CPC ...... G01T 1/2985; G01T 1/185; G01T 1/2935
See application file for complete search history.

(56) References Cited

U.S. PATENT DOCUMENTS 6,011,265 A    1/2000  Sauli

FOREIGN PATENT DOCUMENTS

| JP | 2000504832 | 4/2000 |
|----|------------|--------|
| JP | 2004508544 | 3/2004 |
| JP | 2008243634 | 10/2008 |
| KR | 20020011383 | 2/2002 |
| KR | 20100052074 | 5/2010 |
| KR | 101515130 | 4/2015 |

OTHER PUBLICATIONS

International Search Report—PCT/KR2018/005402 dated Aug. 7, 2018.

*Primary Examiner* — Michael C Bryant
(74) *Attorney, Agent, or Firm* — Cantor Colburn LLP

(57) ABSTRACT

A positron tomography device using a micropattern detector is provided. The positron tomography device comprises: a micropattern gas detection device accelerating electrons so as to generate second ionized electrons; a lead-out strip through which an electrical signal is transmitted by the second ionized electrons; and a signal processing unit for processing the electrical signal detected in the lead-out strip arranged at a predetermined position, wherein a plurality of micropattern gas detection devices is disposed in a ring shape, and the lead-out strip is disposed outside the micropattern gas detection device.

7 Claims, 4 Drawing Sheets

POSITRON TOMOGRAPHY DEVICE USING MICROPATTERN DETECTOR

BACKGROUND OF THE INVENTION

Field of the Invention

The present invention relates to a positron tomography device using a micropattern detector, and more particularly, to a positron tomography device using a micropattern electron amplification means such as a gas electron multiplier (GEM).

Background of the Related Art

Positron emission tomography (PET), also called positron tomography, is one of the nuclear medicine methods using positron emission, and performs the diagnosis of disease and the like through the distribution of radioactive isotopes in the human body by injecting pharmaceutical products, containing the radioactive isotopes which emit positrons, into the human body and then tracking them by using a positron emission tomography device. The positron emission tomography may used to obtain receptor images or metabolic images for evaluation of cancer screening, heart disease, brain disease, and brain function.

Positrons have similar physical properties to electrons with negative charges, but they have positive charges, unlike electrons. These positrons are a type of radiation, are emitted from radioactive isotopes such as C-11, N-13, O-15, and F-18, and since these elements are the main constituents of biological organisms, pharmaceutical products may be produced by using them. The most commonly used pharmaceutical product, F-18-fluorodeoxyglucose (F-18-FDG) is a glucose analog, which, when injected, is much collected at the in-body site where glucose metabolism is accelerated, such as cancer.

FIG. 1 is an exemplary diagram illustrating a positron tomography device according to the related art.

Referring to FIG. 1, the figure A at the left illustrates the isotope emitting positrons and beta+ (β+) collapse. The β+ collapse refers to the reaction of producing neutrons, positrons, and neutrinos due to the collapse of protons in the nucleus. The positron generated at this time produces two photons with 511 keV in the exactly opposite direction while meeting the surrounding electrons to become pair annihilation. This reaction is called annihilation. At this time, the fundamental principle of the PET is to detect two photons, which are emitted, through a pair of detectors. The figure B at the right of FIG. 1 illustrates a PET scan according to the related art.

However, the positron tomography device according to the related art, which is the large-scale equipment produced to scan the entire human body, costs billions of won, and accordingly, is not suitable for use in lab mice used in medical and biological laboratories.

That is, since the positron tomography device according to the related art uses a scintillator detector called scintillator which detects radiation and a Photo Multiplier Tube (PMT) which amplifies the same, there are drawbacks in that the price thereof is expensive, and the size thereof is also large.

SUMMARY OF THE INVENTION

The present invention is derived to meet the aforementioned demands of the related art, and an object of the present disclosure is to provide a compact positron tomography device which may be applied to lab mice.

Another object of the present disclosure is to provide a low-end compact positron tomography device using a device which replaces the conventional scintillator (scintillator detector) and a Photo Multiplier Tube (PMT).

Still another object of the present disclosure is to provide a compact positron tomography device utilizing a GEM detector.

A positron tomography device according to an aspect of the present disclosure for achieving the objects comprises micropattern gas detection devices which generate second ionized electrons by accelerating electrons, a lead-out strip through which an electrical signal by the second ionized electrons is delivered, and a signal processing unit which processes the electrical signal which is detected by the lead-out strip arranged at a predetermined position, and a plurality of the micropattern gas detection devices are disposed in ring shapes, and the lead-out strip is disposed at the outermost of the micropattern gas detection devices.

In an embodiment, the micropattern gas detection devices are disposed in a plurality of ring shapes with different trajectories from each other at predetermined intervals so as to enable the redundant detection of the radiation.

In an embodiment, the micropattern gas detection device corresponds to a film-type gas electron multiplier (GEM) detector.

In an embodiment, the GEM detector includes a GEM chamber into which the reaction gas flows, an induction electrode which is installed at a side into which the electron flows inside the GEM chamber, at least one GEM foil which is installed to be spaced apart from the induction electrode, and a collection electrode which is installed adjacent to the GEM foil, and connected to the lead-out strip.

In an embodiment, the GEM foil includes numerous holes with a predetermined pattern which are arranged on a flexible circuit board, and generates numerous second ionized electrons by accelerating the electron, passing through the flexible circuit board, within an electric field.

In an embodiment, the signal processing unit includes an analog signal processing unit which amplifies and shapes the electrical signal which is input from the lead-out strip, a digital signal processing unit which converts the electrical signal, processed by the analog signal processing unit, into a digital signal and maps the converted electrical signal in a data memory in real time, and a data acquisition system which fetches data, accumulated in the data memory, to process the data into data necessary for the image processing.

In an embodiment, the analog signal processing unit includes a readout circuit which detects a position of the electron by using the electrical signal which is input from the lead-out strip.

DETAILED DESCRIPTION OF THE PREFERRED EMBODIMENT

Figure 1:
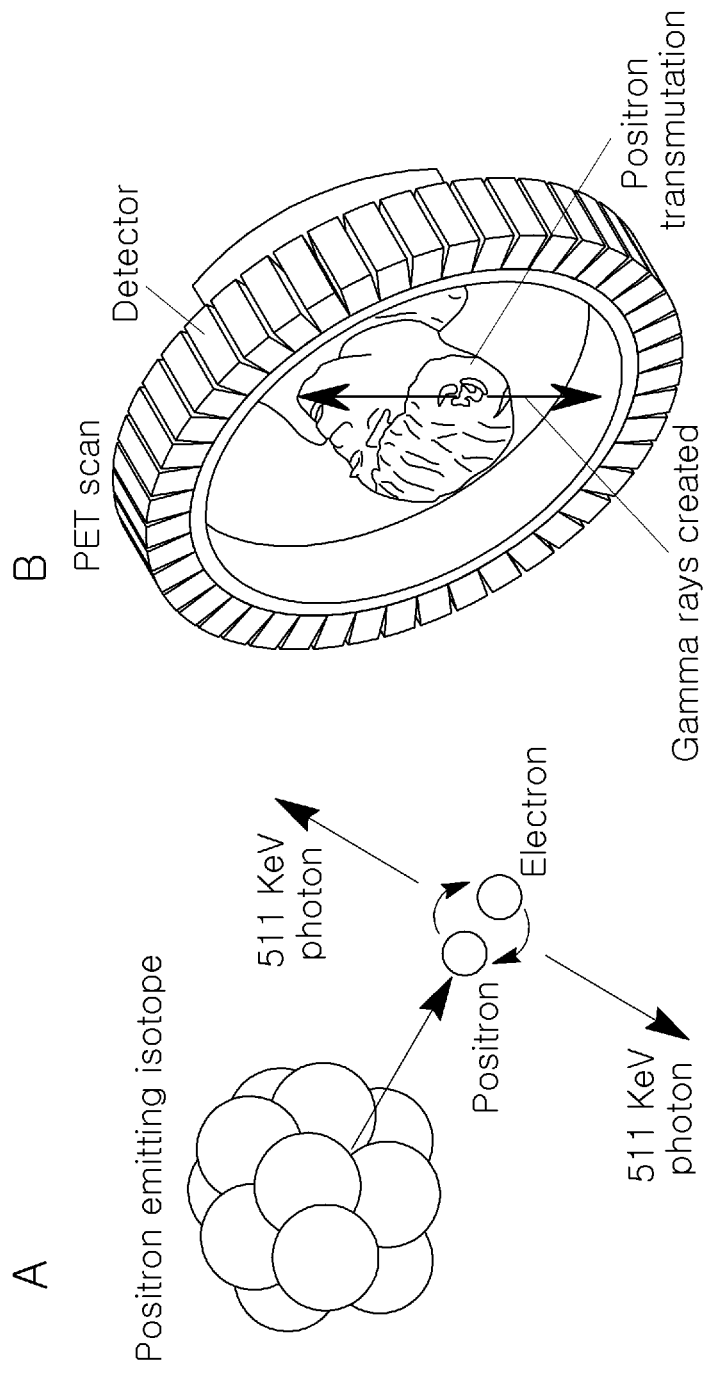
FIG. 1 is an exemplary diagram illustrating a positron tomography device according to the prior art.

Since various changes and numerous embodiments may be made in the present disclosure, particular embodiments will be illustrated in the drawings and described in detail in the detailed description. However, it should be understood that this is not intended to limit the present disclosure to specific embodiments, and the present disclosure includes all changes, equivalents, and substitutes included in the spirit and technical scope of the present disclosure. In describing the drawings, similar reference numerals are used for similar components.

Terms such as first, second, A, and B may be used to describe various components, but the components should not be limited by the terms. The terms are used only for the purpose of distinguishing one component from another component.

For example, a first component may be referred to as a second component, and similarly, the second component may also be referred to as the first component without departing from the scope of the present disclosure. The term and/or includes a combination of a plurality of related and described items or any item of a plurality of related and described items. When a component is said to be "connected" or "coupled" to another component, it should be understood that it may be directly connected to or coupled to another component, but other components may exist therebetween. On the other hand, when a component is said to be "directly connected" or "directly coupled" to another component, it should be understood that there are no other components therebetween.

The terminology used in the present specification is used only for describing particular embodiments and is not intended to limit the present disclosure. Singular expressions include plural expressions unless the context clearly indicates otherwise. In the present specification, it should be understood that the terms "comprise", "having", and the like are intended to indicate that there is a feature, a number, a step, an operation, a component, a part, or a combination thereof described in the specification, and do not exclude the possibility of the presence or the addition of one or more other features, numbers, steps, operations, components, parts, or a combination thereof.

Hereinafter, preferred embodiments according to the present disclosure will be described in detail with reference to FIGS. 2 to 7.

Figure 2:
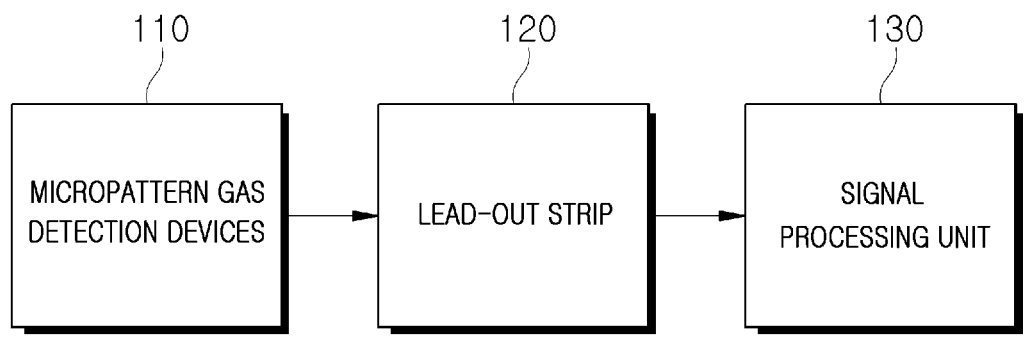
FIG. 2 is a block diagram of a positron tomography device according to an embodiment of the present disclosure.

FIG. 2 is a block diagram of a positron tomography device according to an embodiment of the present disclosure.

Referring to FIG. 2, a positron tomography device 100 according to an embodiment of the present disclosure includes a micropattern gas detection device 110, a lead-out strip 120, and a signal processing unit 130.

The micropattern gas detection device 110 may be implemented by periodically arranging capacitors having a size of several tens of micrometers. When a high voltage is applied to a microcapacitor filled with a suitable gas, each capacitor serves as a Geiger instrument to operate like a high density integrated radiation detector array.

The micropattern gas detection device 110 may be implemented by using a film-type gas electron multiplier (GEM) detector.

The GEM detector 110 may be referred to as a gas electron multiplier. This corresponds to a photo-multiplier or a Photo Multiplier Tube which amplifies the number of photons. The GEM detector 110 may be regarded as a kind of gas detector in that gas is used as a medium for detecting particles.

The GEM detector 110 was devised for the first time as a sensor configured to track the trajectories of small particles in the field of high energy particle physics at the European Organization for Nuclear Research (CERN) in recent years. As compared to the existing other gas detectors, this amplifier has excellent operational properties in various aspects such as spatial resolution, temporal resolution, and detection efficiency.

The GEM detector 110 is a kind of gas ionization detector which detects radiation based on the second ionized charges generated when the particle or the radiation ionizes gas particles.

An electrical signal by the second ionized electrons is delivered to the lead-out strip 120. The lead-out strip 120 is arranged at the outermost of the GEM detectors 110 which are arranged in ring shapes. Particularly, the lead-out strip 120 may be arranged for each channel through which the second ionized charges amplified by the GEM detector 110 are delivered.

The signal processing unit 130 processes the electrical signal which is detected by the lead-out strip arranged at a predetermined position.

Particularly, a plurality of micropattern gas detection device 110 may be disposed in ring shapes, and the lead-out strip 120 may be disposed outside the micropattern gas detection device 110. By adjusting the number of lead-out strips 120, it is possible to adjust the resolution of the output image.

Hereinafter, the arrangement of the GEM detectors will be described in detail.

Figure 3:
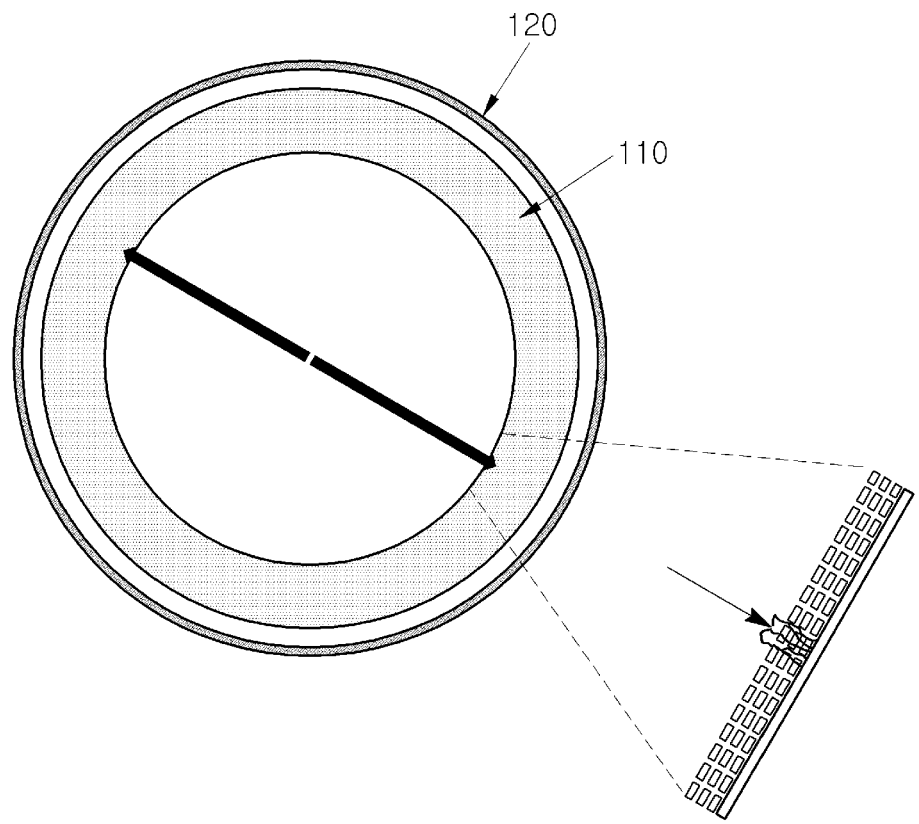
FIG. 3 is a cross-sectional diagram of the positron tomography device according to an embodiment of the present disclosure.

FIG. 3 is a cross-sectional diagram of the positron tomography device according to an embodiment of the present disclosure.

Referring to FIG. 3, the plurality of GEM detectors 110 are arranged in a ring shape, and the lead-out strip 120 is arranged at the outermost of the micropattern gas detection devices in ring shapes. In FIG. 3, the GEM detectors 110 are arranged, for example, in three layers. However, the number of layers in which the GEM detectors 110 are arranged is not limited thereto, and a plurality of ring-shaped GEM detectors 110 each formed of a plurality of layers may be gathered to form a cylinder.

The detector according to the related art is formed of one layer, and the human body is needed to be moved inside the detector due to the arrangement of the detector in the form of a single ring. That is, since the detector according to the related art is insufficient to cover the radiation of the photon due to the narrow cross-sectional area caused by that arrangement, the human body is needed to be moved and scanned. Accordingly, photons which get out of the detector may occur based on the moving speed of the human body.

The GEM detectors 110 which are included in the positron tomography device 100 according to the present embodiment may be arranged in a cylindrical shape. Particularly, the GEM detectors 110 may be arranged in a plurality of ring shapes by varying the trajectories to be arranged as a plurality of layers. The GEM detectors 110 which are arranged in the plurality of layers may increase an amplification rate of second ionized electrons which are generated by photons. In addition, the GEM detectors 110 arranged in the plurality of layers enables the redundant detection of the radiation, and may easily track the moving path of the photon. Here, the redundant detection means that the second ionized electrons generated by one photon are detected along the moving path of the photons.

In addition, the lab mice or the like may be scanned without being moved by the GEM detector 110 arranged in a cylindrical shape. Accordingly, by scanning the inspection target without moving the inspection target, the electrical signal analysis over time may be simplified and the error thereof may be reduced as compared to when the inspection target is moved.

Figure 4:
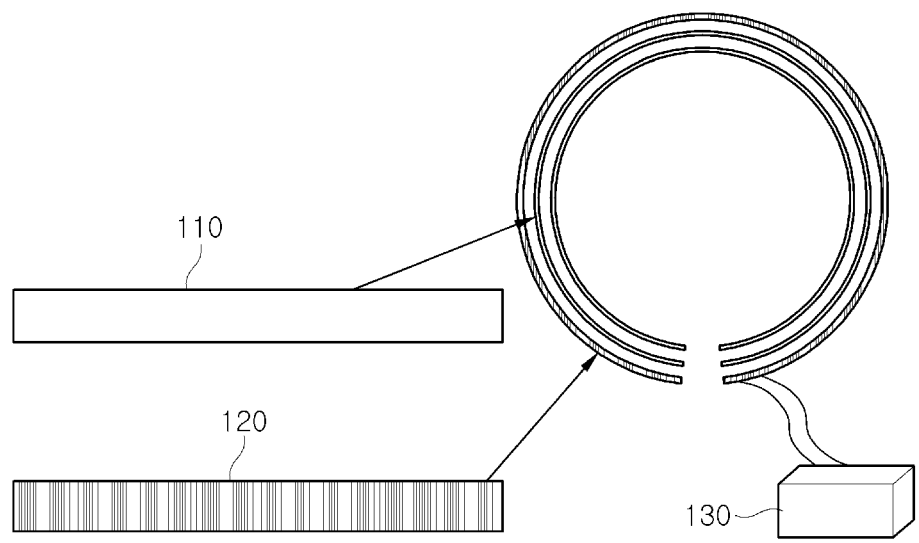
FIG. 4 is an exemplary diagram illustrating the arrangement of a GEM detector of the positron tomography device according to an embodiment of the present disclosure.

FIG. 4 is an exemplary diagram illustrating the arrangement of the GEM detector of the positron tomography device according to an embodiment of the present disclosure.

Referring to FIG. 4, the strip-shaped GEM detector 110 may be arranged in a ring shape. That is, it is also possible to implement the GEM detector 110 in a single band shape instead of using a plurality of existing GEM detector 110 modules. Referring to FIG. 4, the band-shaped GEM detector 110 formed of two layers is exemplarily illustrated. In addition, the lead-out strip 120 is arranged at the outermost thereof. The lead-out strip 120 is connected to the signal processing unit 130.

Hereinafter, the components of the GEM detector 110 will be described in detail.

Figure 5:
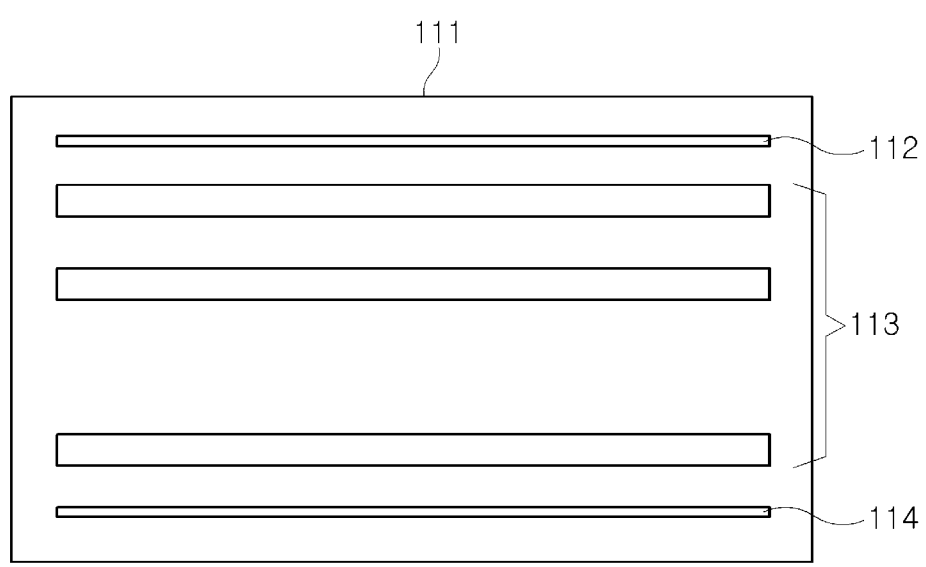
FIG. 5 is a block diagram of the GEM detector according to an embodiment of the present disclosure.

FIG. 5 is a block diagram of the GEM detector according to an embodiment of the present disclosure.

Referring to FIG. 5, the GEM detector 110 includes a GEM chamber 111, an induction electrode 112, a GEM foil 113, and a collection electrode 114. In addition, the GEM detector 110 may further include a voltage generator configured to apply a voltage to the electrodes 112, 114 and the GEM foil 113 and a gas circulator configured to inject and recover gas into the GEM chamber 111.

The GEM chamber 111 includes the induction electrode 112, the GEM foil 113, and the collection electrode 114 therein. The reaction gas flows into the GEM chamber 111. The induction electrode 112 corresponds to a cathode, and the collection electrode 114 corresponds to an anode.

The induction electrode 112 is installed to the side into which electrons flow inside the GEM chamber 111.

The GEM foil 113 is installed to be spaced apart from the induction electrode 112. Particularly, a plurality of GEM foils 113 may be installed to increase the amplification rate of electrons.

The GEM foil 113 has a plurality of holes with a predetermined pattern which are arranged in a flexible circuit board, and generates numerous second ionized electrons by accelerating the electrons, passing through the flexible circuit board, within an electric field.

Specifically, the GEM foil 113 is a flat plate in which a metal layer, for example, such as copper, is thinly formed on each of both surfaces of a thin insulator substrate with a thickness of several tens to several hundreds of micrometers on which many holes with a diameter of several tens of micrometers and an interval of several tens to several hundreds of micrometers are perforated. The insulator substrate may be made of, for example, a Kapton material. The Kapton material is widely used as insulators because the Kapton material has the stable and excellent insulation performance from cryogenic temperature of −269° C. to high temperature of 400° C. When voltages having different magnitudes are applied to the two metal layers of the GEM foil 113, respectively, a strong electric field is formed in the holes while the electric field between a cathode electrode and an anode electrode is concentrated among the holes, and the drift electrons released from the gas particles by the radiation are accelerated by the electric field between the cathode and the GEM foil to approach the holes and suddenly encounter a high-density electric field, causing an electron avalanche in which large quantities of electrons are released from the gas particles.

Since the number of electrons is suddenly increased by the electron amplification phenomenon, it is easy to be electrically detected by a readout circuit. The plurality of GEM foils 113 may be arranged side by side to cause the electron amplification phenomenon several times before the electrons reach the readout circuit.

The conventional gas ionization detector has the poor detection performance because a ratio at which the ionized charge reaches the cathode is low, but the GEM detector 110 may include one or more GEM foils 113 within the gas chamber to amplify the number of charges, thereby improving the detection performance.

The collection electrode 114 is installed adjacent to the GEM foil 113, and connected to the lead-out strip 130.

Typically, the GEM detector needs to apply −2000 V to the cathode, which is the induction electrode 112, and a high voltage having different levels to the two metal layers of the GEM foil, respectively, and there need many peripherals for filling the gas in which argon (Ar) and carbon dioxide ($CO_2$) are mixed at 8:2 within the chamber.

The flat plate used for the GEM detector has a structure in which a copper film having a thickness of 5 to 10 micrometers is stacked on each of both surfaces of a Kapton film having a thickness of about 50 to 70 micrometers. Here, the photolithography technology and the etching technology which are used in the semiconductor process are used to perforate holes having a thickness of about 50 to 70 micrometers. The microholes may be periodically produced through such a micro process, and the produced GEM flat plate appears almost translucent. Unless the GEM flat plate has many microholes, the GEM flat plate has virtually the same structure as a Flexible Printed Circuit Board (FPCB), that is, the flexible circuit board which connects among components in various electronic devices.

A gas gain of the GEM detector depends on the diameter of the microhole and the thickness of the insulator. The smaller the diameter of the microhole, the larger the magnitude of the electric field in the microhole. As the thickness of the insulator increases, the path in which the electron avalanche is deployed within the microhole becomes deeper, and a larger gas gain is obtained.

Figure 6:
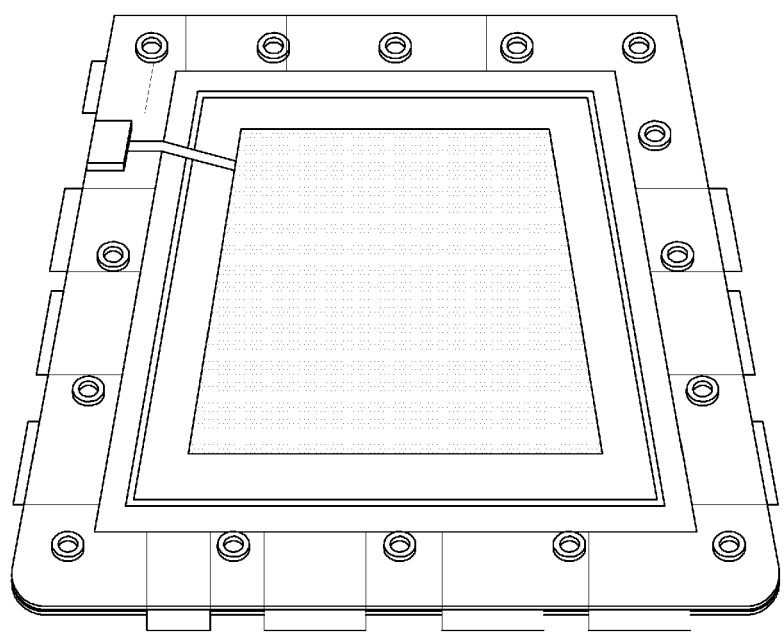
FIG. 6 is an exemplary diagram of the GEM detector which may be employed in the positron tomography device according to an embodiment of the present disclosure.

FIG. 6 is an exemplary diagram of the GEM detector which may be employed in the positron tomography device according to an embodiment of the present disclosure.

Referring to FIG. 6, a single GEM detector module having a square shape is illustrated. The positron tomography device according to the present embodiment may be configured by arranging a plurality of GEM detector modules.

Figure 7:
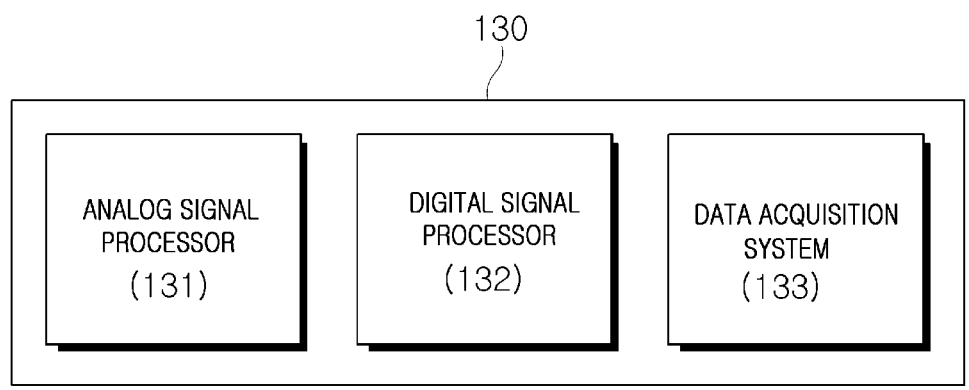
FIG. 7 is a block diagram of a signal processing unit which may be employed in the positron tomography device according to an embodiment of the present disclosure.

FIG. 7 is a block diagram of a signal processing unit which may be employed in the positron tomography device according to an embodiment of the present disclosure.

Referring to FIG. 7, the signal processing unit 130 of the positron tomography device 100 according to an embodiment of the present disclosure includes an analog signal processing unit 131, a digital signal processing unit 132, and a data acquisition system 133.

The analog signal processing unit 131 amplifies and molds the electrical signal which is input from the lead-out strip 120. For example, the analog signal processing unit 131 may include a readout circuit which detects positions of electrons by using the electrical signal which is input from the lead-out strip 120.

That is, the analog signal processing unit 131 may track two photons which are generated by the β+ collapse. That is, by comparing the electrical signals of the pulse which is generated by the second ionized electron cloud generated by the photons, the analog signal processing unit 131 may read the pulses caused by the two photons of the specific collapse, thereby tracking back the position of the collapse.

In addition, the analog signal processing unit 131 may directly read the position of the positron by using the electrical signal of the pulse which is generated by the second ionized electron cloud caused by the positron before the positron is collapsed.

The digital signal processing unit 132 converts the electrical signal, processed by the analog signal processing unit 131, into a digital signal and maps the converted electrical signal in a data memory in real time.

The data acquisition system 133 fetches the data, accumulated in the data memory, to process the data into data necessary for the image processing. That is, the data acquisition system 133 may read out data, accumulated in the data memory, to output the image, which is processed through the image processing, through a display device or the like.

By using the positron tomography device according to the present disclosure as described above, it is possible to produce the compact positron tomography device. That is, it is possible to provide the positron tomography device having a new structure in which at least one layer of the micropattern electron amplifier using the principle of the electron gas multiplier is arranged in the form of the circular band, and the lead-out strip is arranged at the outside thereof.

In addition, according to the present disclosure, it is possible to enhance the radiation detection effect by using the GEM detectors which are arranged in the plurality of ring shapes. That is, it is possible to adjust the resolution very easily based on the number of lead-out strips.

In addition, according to the present disclosure, it is possible to produce the low-end compact positron tomography device which may be applied to the lab mice. Accordingly, the positron tomography device may be used very efficiently in the medical laboratory, the biological laboratory, and the like as well as the clinic and the large hospital.

Although the present disclosure has been described above with reference to the preferred embodiment of the present disclosure, those skilled in the art will understand that the present disclosure may be modified and changed variously without departing from the spirit and scope of the present disclosure recited in the following the claims.

What is claimed is:

1. A positron tomography device, comprising:
    two or more micropattern gas detection devices which generate second ionized electrons by accelerating electrons, wherein each of the two or more micropattern gas detection devices has a cylindrical shape, and wherein the two or more micropattern gas detection devices are arranged in a concentric form and spaced apart from each other at a predetermined interval and with different trajectories to thereby enable a redundant detection of radiation;
    a lead-out strip disposed around the two or more micropattern gas detection devices, wherein the second ionized electrons is delivered to the lead-out strip and the lead-out strip generates an electrical signal by the second ionized electrons delivered thereto; and
    a signal processing unit coupled to the lead-out strip, wherein the signal processing unit processes the electrical signal generated by the lead-out strip.

2. The positron tomography device according to claim 1, wherein the two or more micropattern gas detection devices comprise a film-type gas electron multiplier detector.

3. The positron tomography device according to claim 2, wherein the film-type gas electron multiplier detector comprises:
    gas electron multiplier chamber into which a reaction gas flows;
    at least one gas electron multiplier foil disposed inside the gas electron multiplier
    an induction electrode disposed at one side of the at least one gas electron multiplier and spaced apart from the at least one gas electron multiplier foil; and
    a collection electrode disposed at the other side of the at least one gas electron multiplier and connected to the lead-out strip.

4. The positron tomography device according to claim 3, wherein the at least one gas electron multiplier foil comprises numerous holes with a predetermined pattern.

5. The positron tomography device according to claim 3, wherein the at least one gas electron multiplier foil comprises: two or more gas electron multiplier foils.

6. The positron tomography device according to claim 1, wherein the signal processing unit comprises:
    an analog signal processing unit which amplifies and shapes the electrical signal;
    a digital signal processing unit which converts the amplified and shaped electrical signal, into a digital signal and maps the digital signal in a data memory in real time; and
    a data acquisition system which reads out data from the data memory to process the data into data necessary for an image processing.

7. The positron tomography device according to claim 6, wherein the analog signal processing unit comprises a readout circuit which detects a position of electron by using the electrical signal.

\* \* \* \* \*